United States Patent [19]

Müller

[11] Patent Number: 4,785,764

[45] Date of Patent: Nov. 22, 1988

[54] APPARATUS FOR RECEIVING AND STORING USEFUL ORGANISMS AND PROCESS FOR THE PRODUCTION THEREOF

[75] Inventor: Hans-Rudolf Müller, Zürich, Switzerland

[73] Assignee: Zucher Beuteltuchfabrik AG, Ruschlikon, Switzerland

[21] Appl. No.: 871,104

[22] Filed: Jun. 5, 1986

[30] Foreign Application Priority Data

Jun. 6, 1985 [CH] Switzerland ............... 2407/85

[51] Int. Cl.⁴ ............................................. A01K 1/00
[52] U.S. Cl. ........................................ 119/15; 119/17
[58] Field of Search ................. 119/15, 17; 220/371, 220/372; 215/248, 308

[56] References Cited

U.S. PATENT DOCUMENTS

| | | | |
|---|---|---|---|
| 836,174 | 11/1906 | Bauer | 220/371 |
| 3,083,861 | 4/1963 | Amberg et al. | 220/371 |
| 3,272,376 | 9/1966 | Tierney et al. | 119/17 X |
| 3,396,701 | 8/1968 | Trexler | 119/15 |
| 3,468,289 | 9/1969 | Broida | 119/15 |
| 4,215,649 | 8/1980 | Vorbeck | 119/15 |
| 4,355,111 | 10/1982 | Shimizu et al. | 215/248 X |

Primary Examiner—David A. Scherbel
Assistant Examiner—Creighton Smith
Attorney, Agent, or Firm—Helfgott & Karas

[57] ABSTRACT

A casing in the form of cylindrical hollow body is terminated at one end by a base and is optionally provided with a hanger. The other end of the cylindrical hollow body is covered by a cover. The cover has a gauze arranged in a frame. The gauze meshes have a clearly defined cross-sectional surface. Useful organisms are placed in a protected manner in the hollow body and only those useful organisms having a desired size can pass through the gauze. The casing is treated by chemical or physical means so that it will remain intact and the organisms contained therein will be protected for a time period predetermined by such treatment. As the casing is made from non-toxic materials, its decomposition at the end of the intactness period does not adversely effect the environment.

8 Claims, 1 Drawing Sheet

APPARATUS FOR RECEIVING AND STORING USEFUL ORGANISMS AND PROCESS FOR THE PRODUCTION THEREOF

BACKGROUND OF THE INVENTION

The present invention relates to an apparatus for receiving and storing organisms used to favorably influence the environment, particularly by the control and destruction of harmful bacteria and other harmful organisms, as well as harmful materials, the useful organisms being placed in a casing having an opening.

Until recently the control of harmful bacteria and other harmful organisms, as well as harmful materials, e.g. harmful waste materials, has almost exclusively been accomplished through the use of chemical agents. Although chemical agents are very effective, their secondary effects on the environment are becoming increasingly unacceptable. Consequently, much effort is now being exerted to control bacterial and other harmful organisms, as well as harmful materials, in a manner such that detrimental effects on the environment are avoided to the greatest possible extent.

One application of the present type, which appears to have a good chance of success, is the use of useful organisms, i.e. organisms able to eliminate pests of all types or harmful material and the like, or able to at least reduce or even neutralize their harmful action.

The use of useful organisms presupposes that they can be used at a time when their activity, and therefore their action, is at a maximum, or when the pests or harmful substances can best be influenced or destroyed. The useful organisms are generally sensitive, living organisms and must be kept under favorable living conditions.

SUMMARY OF THE INVENTION

The aim of the present invention is to provide an apparatus of the aforementioned type which affords optimal conditions for the evolution and timely use of the useful organisms stored therein while ensuring that the apparatus has no detrimental effect on the environment.

The apparatus of the present invention comprises a hollow casing having at least one wall. The casing is provided with a cover having at least one opening the cross-sectional surface dimensioning of which is suitably adjusted to influence the behavior of organisms placed in the casing. As a result, adequate protection is provided for the growth of the useful organisms and the dimensioning is such that there is a selection with respect to the size of such organisms.

BRIEF DESCRIPTION OF THE DRAWINGS

The present invention will now be described in greater detail with reference to certain embodiments which are offered to illustrate the invention and not to limit same and with reference to the attained drawings in which.

DETAILED DESCRIPTION OF THE PREFERRED EMBODIMENTS

The present invention is based on the idea that organisms useful for controlling pests and harmful substances must be given adequate protection and must be made available in a favorable time period. FIGS. 1 to 9 show examples of apparatuses permitting the optimal use of the useful organisms.

Figure 1:
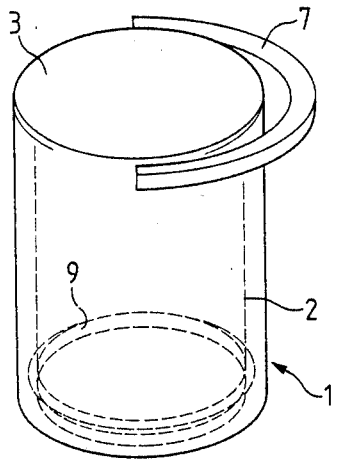
FIG. 1 is a front plan view of a cylindrical casing having a hanger and cover which has calibrated openings.

As shown in FIG. 1, casing 1 is constructed as a cylindrical hollow body 2. Body 2 is terminated at one end by a base 3. A cover 4 is mounted from the other end of body 2. In the embodiment of FIG. 1, cover 4 is constructed as a sieve. Cover 4 is comprised of a circular frame 6 and a gauze 5 having a defined mesh size. Gauze 5 is fixed in circular frame 6. Frame 6 has an annular projection 8 on its circumferential surface.

Useful organisms or the broth of such useful organisms are introduced into the cavity of casing 1 which is then closed with cover 4. As a result of the clearly defined mesh size, only those useful organisms having a smaller body cross-section than the cross-sectional surface of the mesh size can leave the casing 1. Casing 1 also provides adequate protection for the useful organisms. As shown in FIG. 1, to enable casing 1 to be positioned at the point of use with a downwardly directed cover 4, a hanger 7 is mounted on casing 1. Hanger 7 can be bow shaped, as shown in FIG. 1, or any other shape. Hanger 7 can also be mounted from base 3.

Casing 1 may be made of plastic. To ensure that cover 4 is reliably connected to casing 1, it is inserted in the latter with the aid of a spring catch. The spring catch comprises an annular projection 8 on the circumferential surface of frame 6 of cover 4 and a slot-like offset 9 on the inner wall of hollow body 2. Frame 6 and also the threads of gauze 5 are preferably made of plastic.

It is important to choose for the fabrication of the plastic parts of a plastic which remains intact while the protected organisms are being used and which thereafter decomposes to form products that are not harmful to the environment, e.g. poisons. Polyamide plastics having protein-like structures are suitable.

Casing 1 and cover 4 can be pretreated to ensure that following the end of the use of the useful organisms, the plastic or plastics used do not remain intact for an excessively long period. By means of such pretreatment, which for example can consist of irradiation by ultraviolet, beta or similar rays, it is possible to adjust the life, i.e. the period during which the plastic remains intact. An alternative to irradiation is chemical treatment with, for example, oxidizing chemicals, in order to adjust the life of the plastics of casing 1 and cover 4. In addition to the aforementioned polyamides, it is also possible to use cellulose plastics, polyethylene, polypropylene, polyester and lie plastics which also decompose without detriment to the environment and which have an adjustable life.

Casing 1 can be colored to ensure protection of the useful organisms. For example, a reflective color can be employed. Casing 1 can also be opaque.

FIGS. 2 to 9 show variants, which on the onehand relate to the shape of the casing and on the other the construction of the clearly defined openings.

Figure 2:
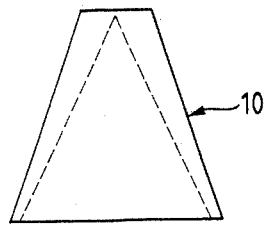
FIG. 2 a side view of a frustum-shaped casing with a cover.

In FIG. 2 the casing is conical or frustum-shaped. The associated cover 11 can have a similar construction to cover 4 of FIG. 1. It can also be injection moldedas a plastic part, the clearly defined openings being provided in the injection.

Figure 3:
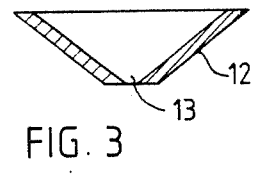
FIG. 3 is a cross-seciton of a conical cover having a calibrated opening.

FIG. 3 diagrammatically shows a conical cover 12, which only has a single clearly defined opening 15.

Figure 4:
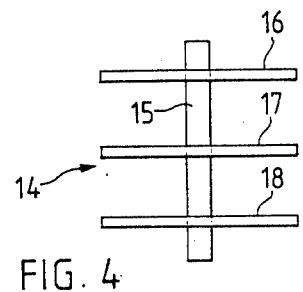
FIG. 4 is a side view of an insert for a casing, the insert having a stage-alike arrangement of different, clearly defined openings.

FIG. 4 diagrammatically shows a multiple over 14 inserted, as an insert, in casing 1 and which comprises a rod-like holder 15 and a plurality, three in FIG. 4, of disk-shaped covers 16, 17, 18. The covers 16, 17, 18 have clearly defined (not shown) openings. It is possible to provide openings of different sizes in each of covers 16, 17, and 18. If cover 16 is the inner cover, it can have the smallest openings, e.g. approximately 100 $\mu$m, while covers 17, 18 towards the outside have increasingly large openings, e.g. up to approximately 500 $\mu$m.

Figure 5:
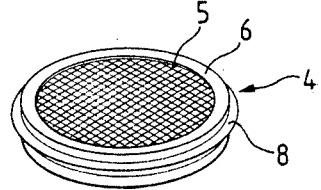
FIG. 5 is a cross-section of a lid-like casing cover pr with a gauze of defined mesh size.

FIG. 5 shows the cover 4, as it is employed in casing 1 of FIG. 1. Gauze 5, having clearly defined mesh size, is embedded in the plastic, injection molded frame 6. Projection 8 of the spring catch or snap mechanism is clearly shown on the outer circumference of frame 6.

Figure 6:
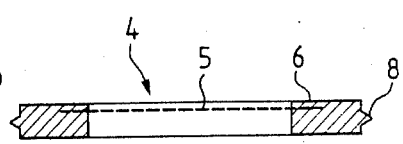
FIG. 6 is a cross-section of another embodiment of a casing cover having clearly defined openings.

FIG. 6 shows a plastic injection molded cover 19 having clearly defined openings 13 arranged therein. Openings 13 are located at the end of conically tapering depressions 21.

Figure 7:
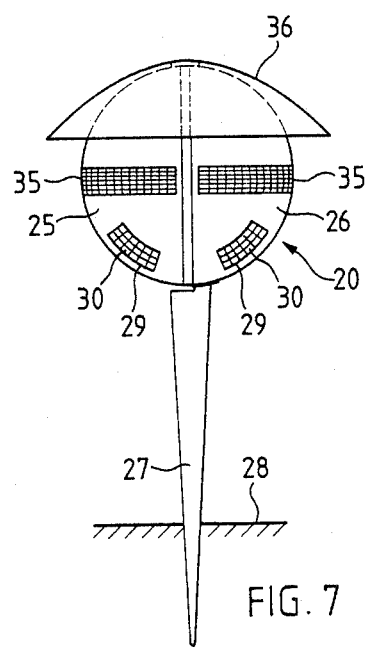
FIG. 7 is a side view of a spherical casing provided with an insert intake and sunshade.
Figure 9:
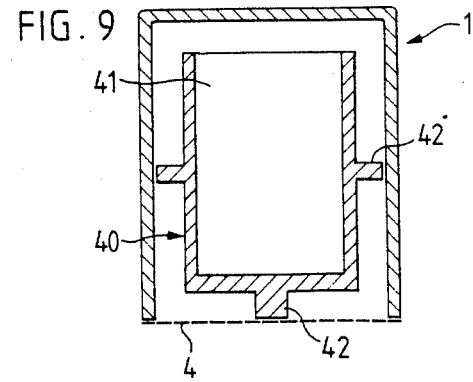
FIG. 9 is a cross-section of a cylindrical casing provided with a hollow, cylindrical insert.

FIG. 7 shows a spherical casing 20, which is assembled from two joined half-shells 25, 26. The joining of the two hemispherical shells 25, 26 can be facilitated by a snap connection or catch, as is described in conjunction with FIG. 1. Half-shell 26 is provided with a stake 27, with which the casing can be introduced into the ground 28. The stake can be replaced by a tripod or stand enabling the casing to be set upright. Half-shells 25, 26 have wall parts 29 with covers 30. Covers 30 are e.g. constructed in accordance with the embodiments of FIGS. 5 and 6. While covers 30 are located on the lower half of casing 20, windows 35 are provided in the vicinity of the largestr diameter and serve to ventilate the cavity of casing 20. Windows 35 are covered with a gauze whose mesh size is smaller than that of covers 30.

Figure 8:
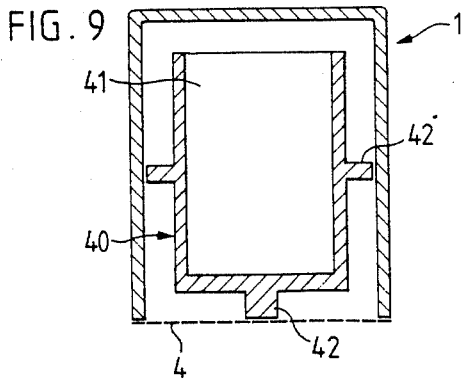
FIG. 8 is a cross-section of another embodiment of a casing sunshade.

As is shown in FIG. 7, a sunshade 36 may be employed as a further means to protect the useful organisms contained within casing 20. Sunshade 36 spreads in dome-like manner over casing 20 and having a larger diameter than casing 20, projects laterally beyond the same. A similar sunshade 37 is shown in FIG. 8. Sunshade 37 has a leg 38 enabling it to be mounted in spaced manner on casing 20.

FIG. 9 shows a casing 1 according to FIG. 1, in which the cover 4 is only shown diagrammatically and can be constructed according to any one of the aforementioned cover constructions. An insert 40 is placed in casing 1 and is constructed as a housing with a cavity 41. Cavity 41 is adapted to house the useful organisms. The position of insert 40 can be fixed within casing 1 by supports 42.

In place of insert 40, it is also possible to use other insert configurations, e.g. diaphragms or barriers, which enable the interior of the casing to be subdivided without forming clearly defined openings. The latter must be provided in covers of the type such as is shown in FIG. 4.

The described apparatus has the advantage that it gives numerous possibilities for the optimum housing of useful organisms. It is possible to widely vary the shape of the casing, its color and its material. Additional means can also be used to provide further protection, e.g. hangers, sunshades and inserts within the actual casing.

What is claimed is:

1. An apparatus for receiving and storing useful organisms for control or destruction of harmful bacteria, other harmful organisms or harmful materials, comprising a hollow solid casing having an opening, said casing being adapted to receive and store said useful organisms, and a cover having at least one opening which has a dimensionally defined cross-sectional surface, said cover being mounted on the casing so as to close the opening in the casing; the opening in the cover serving to permit exit from the interior of the casing of only those useful organisms smaller than said opening, the casing and cover being formed from a material which decomposes without substantial detriment to the environment and which is selected from the group consisting of polyamide, cellulose, polyethylene, polypropylene, and polyester, said material having been treated prior to use as casing and cover with ultraviolet or beta radiation or with an oxidizing agent for a sufficient period to adjust the period during which the cover and casing will remain intact during use to a desired time so that when subjected to weathering the treated material will remain intact for said desired time and will then break down into products substantially non-detrimental to the environment.

2. The apparatus according to claim 1, wherein the cover has a plurality of said openings which form the meshes of a gauze having clearly defined mesh size.

3. The apparatus according to claim 1, further including means on the cover and cooperating means on the iner surface of the casing for providing a snap-fit closure between the cover and the casing.

4. The apparatus according to claim 1, wherein the casing has a shape having at least one plane of symmetry.

5. The apparatus according to claim 1 wherein the casing is parallelepipedic, cylindrical, conical, spherical, pyramidal, or frustum-shaped.

6. The apparatus according to claim 1 wherein the casing has at least one window for ventiliating the interior of the casing and such window is provided with a cover having a smaller passage than the opening of the cover of the casing.

7. The apparatus according to claim 8, wherein said window is provided with a plurality of such passages and the cover has a plurality of openings which form the meshes of gauze having a clearly defined mesh size.

8. A process for protecting useful organisms used for control or destruction of harmful bacteria, other harmful organisms or harmful material, prior to use of such useful organisms, comprising the steps of:

treating a material selected from the group consisting of polyamides, cellulose, polyethylene, polypropylene and polyesters with ultraviolet or beta irradiation or with an oxidizing agent for a sufficient period to adjust the period during which the (plastic) material will remain intact for said desired time and will then break down into products substantially non-detrimental to the environment;

introducing the useful organisms into a solid hollow container made of such treated material; and restricting the exit of the useful organisms from the container so that only those useful organisms having a desired size may exit.

* * * * *

UNITED STATES PATENT AND TRADEMARK OFFICE
CERTIFICATE OF CORRECTION

PATENT NO. : 4,785,764
DATED : November 22, 1988
INVENTOR(S) : Hans-Rudolf Muller It is certified that error appears in the above-identified patent and that said Letters Patent is hereby corrected as shown below:

On the Title Page, Item [73], "Zucher Beuteltuchfabrik AG" should read
--Zuricher Beuteltuchfabrik AG--.

Signed and Sealed this

Second Day of May, 1989

Attest:

DONALD J. QUIGG

Attesting Officer

Commissioner of Patents and Trademarks